United States Patent [19]
Feuerborn et al.

[11] Patent Number: 5,713,872
[45] Date of Patent: Feb. 3, 1998

[54] FLEXING SAFETY SHIELD FOR HYPODERMIC NEEDLES

[76] Inventors: Arthur Mark Feuerborn, 355 Lantana, #777, Camarillo, Calif. 93010; David John Feuerborn, P.O. Box 498, Camarillo, Calif. 93011

[21] Appl. No.: 767,314

[22] Filed: Dec. 16, 1996

Related U.S. Application Data

[63] Continuation-in-part of Ser. No. 257,352, Jun. 9, 1994, Pat. No. 5,591,133.
[51] Int. Cl.$^6$ ............................................. A61M 5/00
[52] U.S. Cl. ............................................. 604/192; 604/263
[58] Field of Search ............................. 604/192, 198, 604/263, 187, 110

[56] References Cited

U.S. PATENT DOCUMENTS

| | | | |
|---|---|---|---|
| 4,139,009 | 2/1979 | Alvarez | 604/198 |
| 4,867,172 | 9/1989 | Haber et al. | 604/192 X |
| 4,950,250 | 8/1990 | Haber et al. | 604/192 |
| 4,998,922 | 3/1991 | Kuracina et al. | 604/263 X |

*Primary Examiner*—John D. Yasko
*Attorney, Agent, or Firm*—Gene W. Arant

[57] ABSTRACT

A shield for a hypodermic needle assembly includes a hollow plastic sleeve with an elongated main portion adapted to normally enclose the main portion of a needle, a slidable outer end portion which normally extends beyond the tip end of the needle, the elongated main portion of the hollow sleeve responding to an axial force on the outer end portion for expanding radially outwardly to retract the end portion of the sleeve and expose the needle tip end, a spaced pair of circumferential flanges formed on the elongated main portion of the sleeve, and a flexible collar encircling the sleeve and slidable over one of the flanges so as to occupy a position between the flanges and thereby prevent subsequent expansion of the main portion of the sleeve.

14 Claims, 9 Drawing Sheets

FIG. IIA

FIG. IIB

FLEXING SAFETY SHIELD FOR HYPODERMIC NEEDLES

RELATED APPLICATION

This application is a continuation-in-part of our prior application Ser. No. 08/257,352 filed Jun. 9, 1994 and entitled FLEXING SAFETY SHIELD FOR HYPODERMIC NEEDLES; now U.S. Pat. No. 5,591,133.

BACKGROUND OF THE INVENTION

1. Field of the Invention

The apparatus of the present invention relates to hypodermic needles, and more particularly to a shield for hypodermic needles to protect medical personnel and others from accidental contact with needles that may have been exposed to contagious and/or blood-borne diseases.

2. Art Background

Hypodermic needles are indispensable to the health care industry for both drawing bodily fluids from and administering medication to patients. Most hypodermic needles currently in use are disposed of, after one use, in a waste receptacle to limit further contact between medical personnel or patients and the cannulas of the uses needles. Avoiding contact with used needles is essential to prevent the transmission of diseases, particularly blood-borne diseases such as acquired immune deficiency syndrome (AIDS). Although medical personnel are trained to handle used needles with extreme care to avoid exposing themselves, the large volume of unshielded syringes renders such accidental exposure commonplace.

The hypodermic syringes now commonly in use offer insufficient protection against accidental contact with their cannulas after use. The most common hypodermic needle includes a replaceable plastic cap to cover its cannula. The cap is removed just prior to use and is replaced thereafter. The act of replacing the cap exposes medical personnel to the danger of accidental contact, particularly subcutaneous contact, with the used cannula. Moreover, the person administering the needle may forget to replace the cap, or may do so incorrectly, thus increasing the probability of accidental contact between the used cannula and those who must handle medical refuse.

A number of prior art needle shields have been developed in an attempt to solve the problems of accidental exposure and illicit re-use. Many of these devices create a "safe" position with a cylindrical outer sleeve that radially surrounds the cannula such that the cannula is not exposed after use. Many of these designs, however, require that the needle administrator take an affirmative act to place the device in the safe position. These devices suffer from problems similar to those of the common hypodermic needle using a plastic cap. The act of placing the device in the safe position exposes the needle administrator to the danger of accidental contact with the cannula. Moreover, the needle administrator may forget to place the device in the safe position and thus fail to reduce the probability of accidental contact between the cannula and refuse handlers.

Other prior art designs have been developed in an attempt to provide a needle shield that automatically resets to a safe position after the needle is used, thus eliminating the need for an affirmative act by the administrator. These devices also typically employ a sleeve to axially surround the cannula. The cannula is coupled to a spring such that when an axial force of sufficient magnitude is applied by the needle administrator to the syringe, the cannula protrudes from the sleeve to permit injection. The spring develops a reactive axial force in the direction opposite to the applied force. The use of a spring to reset the cannula into the safe position suffers from a major drawback, because the reactive force created by a spring increases as the length of the spring is decreased through compression. Thus, to attain an appropriate depth of insertion in the patient, the needle administrator must apply an increasingly greater force than was required to initially disengage the needle from the safe position. This increasing force will be transmitted to the patient, causing discomfort, and will likely render smooth administration of an injection difficult. This inherent property of springs therefore makes it difficult to solve the problems of inadvertent exposure and unacceptable large resistance during the injection process.

An important prior art concept is that shown in the Alvarez U.S. Pat. No. 4,139,009 issued in 1979. Alvarez employed a plastic sleeve formed into separate longitudinal slats that bow outwardly when an axial force is applied to the forward end of the sleeve. A variation of the Alvarez design is shown in the Kuracina U.S. Pat. No. 4,998,922 issued in 1991.

There is, however, much room for improvement in the art of shielding the handles of hypodermic needles from the cannulas of those needles after they have been used.

SUMMARY OF THE INVENTION

The shield of the present invention is a novel and non-obvious improvement over previous attempts to shield handlers of hypodermic needles from accidental contact with such needles once they are used. The present invention provides a sleeve which is initially configured in a "safe" position. The safe position occurs when the cannula is completely withdrawn inside of the sleeve so that no part of the cannula protrudes from the sleeve. The sleeve's structural characteristics are such that an initial threshold of axial force must be exceeded before the sleeve's initial rigidity is overcome, thereby permitting exposure of the cannula. Once the threshold force is exceeded, the amount of force necessary to further displace the shield of the present invention to expose the cannula to the extent necessary to achieve an appropriate depth within a patient is not substantially greater than (if not less than or equal to) the threshold force, so as to not interfere with the smooth administration of an injection.

According to the invention the needle shield is in the form of a sleeve having longitudinal displaceable portions or slats that hingedly bend at predetermined locations to facilitate their displacement. The threshold axial force is that force necessarily applied to the syringe, with the outer end of the sleeve in contact with the surface to be penetrated, to overcome the initial rigidity of the sleeve and thereby cause the displaceable portions or slats to hinge at the predetermined locations. Once hinging begins, the force necessary for continued displacement of the displaceable portions may actually be less than the threshold force initially required.

During withdrawal of the needle, the elasticity of the sleeve causes the slats or displaceable portions of the sleeve to retract until the sleeve has once again returned to its initially rigid state and the cannula has become completely withdrawn inside of the sleeve. Thus, the shield automatically returns to its "safe" state.

Further according to the invention a locking feature is provided to retain the shield in the safe position. A pair of circumferential flanges are provided at an index location on the sleeve. A slidable collar normally positioned near the

3 inner end of the sleeve may be moved (in a direction opposite to that required to expose the cannula) and locked between the pair of circumferential flanges at the index location on the sleeve. This locking mechanism becomes engaged while the shield is already providing protection via the safe position.

A further preferred feature of the invention is that the collar is flexible, encircles an inner end portion of the sleeve, and is frangibly connected to the inner end portion of the sleeve so that after usage of the needle assembly when the sleeve collapses back to its original shape, the collar may then be detached from the sleeve and slid over one of the flanges so as to occupy a position between the pair of flanges and thereby prevent any subsequent expansion of the sleeve.

It is therefore an objective of the present invention to provide a hypodermic needle shield which requires a threshold axial force, to go from a safe position to an exposed position, that is significantly greater than axial forces typically encountered during most unintentional subcutaneous exposures to used cannulas, but is not so great as to cause abnormal discomfort to a patient during initial insertion.

It is further an objective of the present invention to provide a hypodermic needle shield that, once the threshold force has been exceeded, the force necessary for continued displacement of the shield is less than that which would cause disruptive interference with the injection process.

It is still further an objective of the present invention to provide a hypodermic needle shield which when withdrawn from the patient returns immediately to the safe position.

It is still further an objective of the present invention to provide a hypodermic needle shield which has a locking feature that discourages illicit use after disposal and greatly increases the force necessary to overcome the safe position and to expose a used cannula.

These and other objectives of the present invention will become apparent in light of the following detailed description.

4

DETAILED DESCRIPTION OF THE INVENTION

Figure 1:
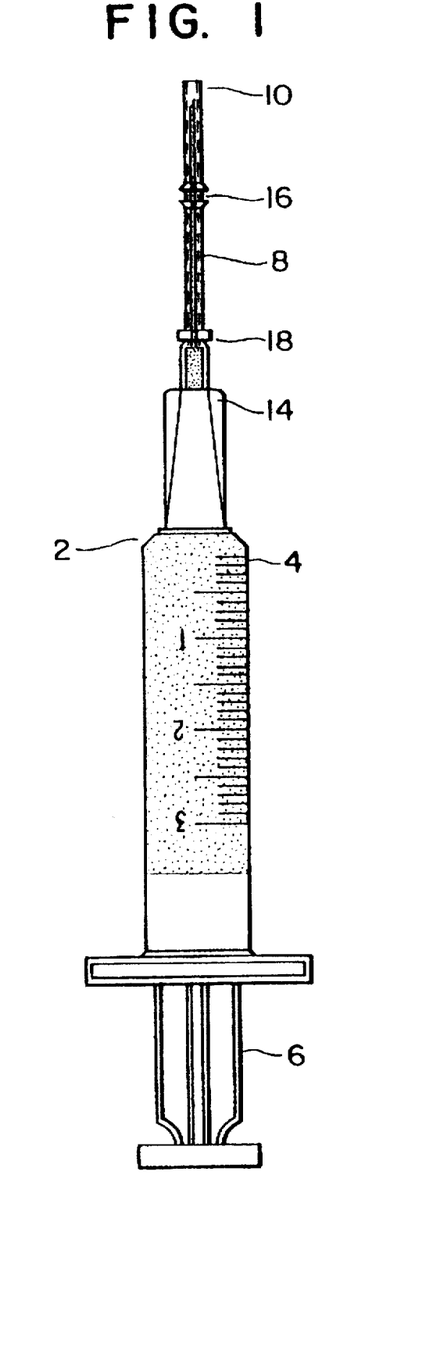
FIG. 1 illustrates a hypodermic needle assembly in conjunction with the needle shield of the present invention.

FIG. 1 illustrates a hypodermic needle assembly 2 in conjunction with the needle shield of the present invention. As shown in FIG. 1, the hypodermic needle assembly 2 includes a syringe barrel 4 housing a portion of a plunger 6. The barrel 4 is coupled to a hub 14 which is coupled to a cannula 8. The needle has a base end, a main portion, and a tip end. As shown in FIG. 1, the needle shield of the present invention includes a cylindrical sleeve 10 which is also coupled to the hub 14.

The sleeve 10 may include a thin membrane at the tip of the sleeve toward the tip end of cannula 8. The membrane would be broken as the cannula 8 protrudes from sleeve 10, such as during insertion into a patient or vial. The membrane can serve several purposes, including hermetically sealing the cannula until a first use. The membrane can also be used to contribute towards the initial threshold force necessary to cause exposure of the cannula. Even after the membrane has been initially pierced, it can continue to provide resistance to axial displacement of the sleeve, thereby contributing towards the requisite threshold force.

The cylindrical sleeve 10 may be coupled to a hub 14 of any size or shape. Further, the sleeve 10 could be manufactured with the hub 14 as one piece. Thus, the needle shield of the present invention may be manufactured to operate with any existing line of hypodermic needles, or it may be customized for integrated manufacture. The manufacturer also has the option to retain the existing overcap and packaging for the needle.

In the preferred embodiment, the sleeve 10 is made from POLYPROPYLENE. The sleeve may also be made of JDPE, LDPE, DELRIN, NYLON or any materials providing the desired mechanical characteristics as disclosed herein.

Figure 2:
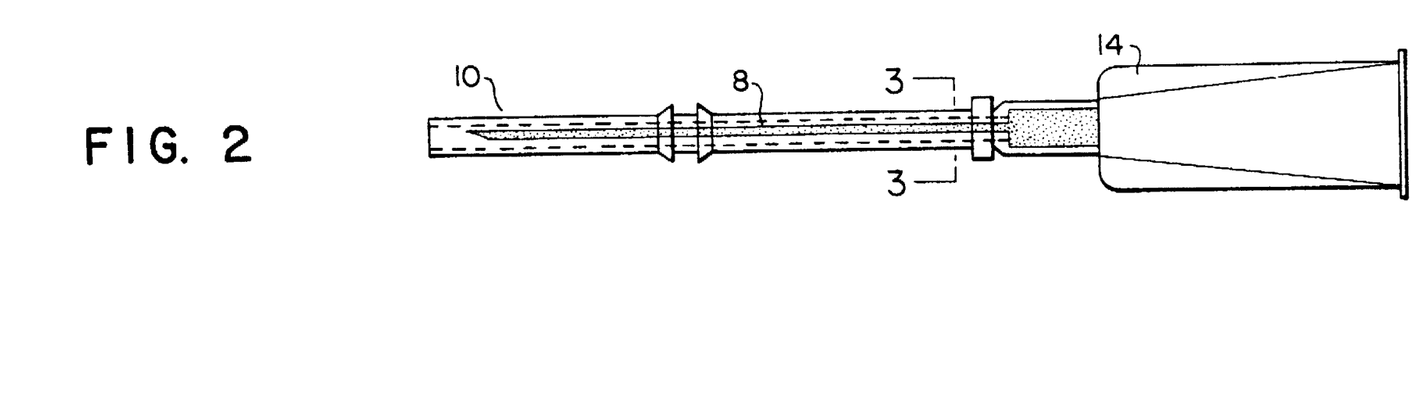
FIG. 2 illustrates the needle shield of the preferred embodiment of the present invention in the safe position.
Figure 3:
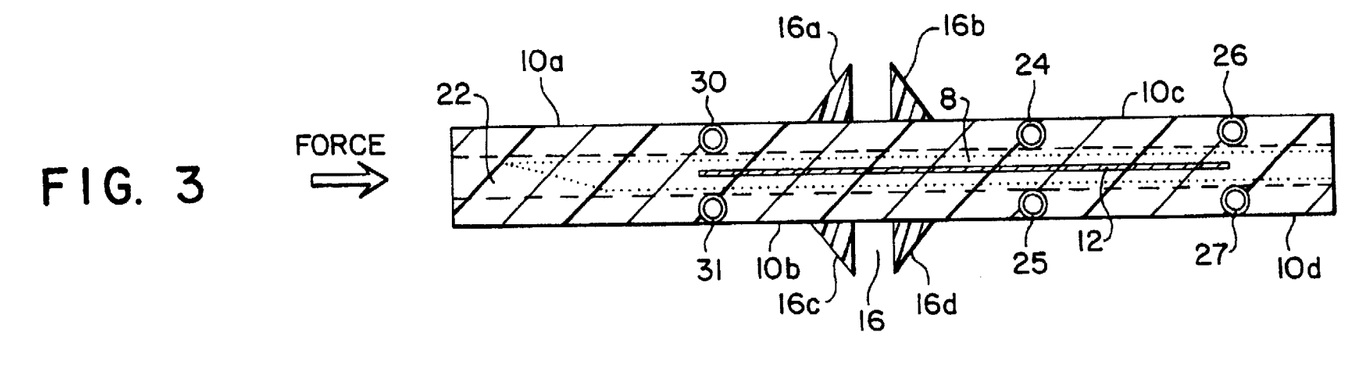
FIG. 3 is an exlarged longitudinal cross sectional view along lines A—A of FIG. 2.

FIG. 2 illustrates the needle shield of the present invention in the safe position, the cannula 8 being then completely housed within the cylindrical sleeve 10. FIG. 3 illustrates a longitudinal cross-sectional view taken along lines A—A of FIG. 2. The cylindrical sleeve 10 is preferably a unitary plastic member that defines an axially extending central bore 22 to slidably receive the cannula 8. The cylindrical sleeve 10 includes a radially rigid outer end portion 10a which is at least coextensive with the tip of the cannula when the shield is in the safe position, a radially rigid inner end portion 10d, and displaceable portions 10b and 10c. In the preferred embodiment, the displaceable portions or slats 10b and 10c are formed by creating two slits 12 along the length of the cylindrical sleeve 10 between outer end portion 10a and inner end portion 10d. The slits 12 are preferably separated by 180 degrees around the sleeve 10. Thus, each end portion 10a, 10d is preferably cylindrical in shape while the slats 10b, 10c are semi-cylindrical.

Displaceable portions or longitudinal slats 10b and 10c, each has two subportions. One subportion of the displaceable portion or slat 10b is hinged at or adjacent to its interface with the outer end portion 10a of the sleeve at 31, while its other subportion is hinged at or adjacent to the interface with the inner end portion 10d of the sleeve at 27. In similar fashion one subportion of the displaceable portion or slat 10c is hinged at or adjacent to its interface with the outer end portion 10a of the sleeve at 30, while its other subportion is hinged at or adjacent to the interface with the inner end portion 10d of the sleeve at 26. At a longitudinal mid-region of the sleeve 10 the two subportions of slat 10b are hinged at 25, and the two subportions of slat 10c are similarly hinged at 24 at the longitudinal mid-region.

The slits 12 may completely sever the cylindrical sleeve 10, or may be formed such that a thin layer of plastic remains along the length of the slit. It will be appreciated by those of skill in the art that more than two slits may be formed in sleeve 10 and that the slits may be arranged at various angles around the sleeve 10 to attain the desired initial rigidity characteristics of the sleeve 10, as well as the desired force vs. displacement response of the sleeve once the threshold has been exceeded. The number of slits will of course govern the number of subportions making up each displaceable portion 10b and 10c.

Figure 4:
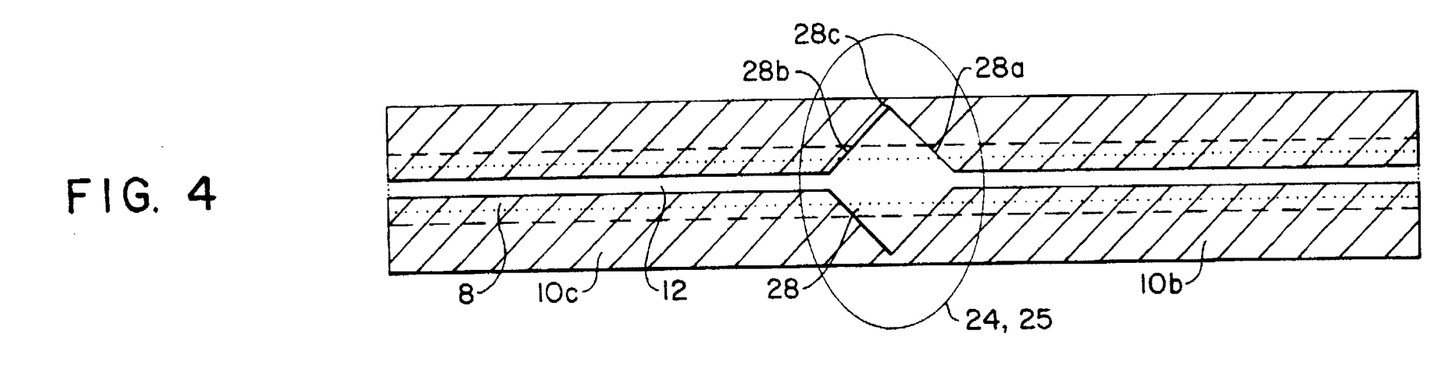
FIG. 4 is an enlarged and exploded fragmentary cross-sectional view of a hinging portion that joins displaceable portions of a sleeve of the present invention.

FIG. 4 illustrates an enlarged and exploded longitudinal cross-sectional view of the longitudinal mid-region of sleeve 10, although circumferential flanges 16 are not shown here. In one preferred embodiment, hinges 24, 25 are formed by creating a triangular indentation 28 in the cylindrical sleeve 10. The base of the triangular indentation is the edge of the sleeve formed by the slit. The indentation can be formed during the manufacturing of the sleeve 10, or by deforming or cutting the material comprising sleeve 10.

The hypodermic needle assembly 2 remains in the safe position until a sufficiently large reactive axial force is created at outer end portion 10a of the sleeve 10, as shown in FIG. 3, to overcome the initial rigidity of sleeve 10. The axial force on outer end portion 10a results from the needle administrator placing the tip end of the sleeve 10 in contact with the patient and applying force to the needle assembly 2. The axial force is the reaction force created by the patient's body and is transmitted axially along the sleeve 10 and applied along the sides "a" of the triangular indentation 28 of the hinges 24, 25 as shown in FIG. 4. The force on side 28a creates a torque around an apex 28c of the triangular indentation 28. Additionally, the axial force applied to the apex 28c creates a torque around hinges 30, 31, and 26, 27. Because the plastic sleeve 10 does not substantially deform axially, the axial force is opposed by an equal axial force directed opposite to the applied axial force.

When the applied axial force exceeds a threshold axial force dictated by the geometry, dimensions and materials of the sleeve 10, the resulting torque causes the subportions of displaceable portions or slats 10b and 10c of the sleeve 10 to be displaced radially away from the cannula 8 about hinges 26, 27 and 30, 31. Once the threshold axial force has been exceeded, very little additional force (if any) is necessarily applied to needle assembly 2 to cause further displacement of displaceable portions 10b and 10c. This is because relatively little compression of hinges 24, 25, other than that caused by the threshold axial force, results from the radial displacement of the subportions of slats or displaceable portions 10b and 10c of the sleeve 10.

Figure 5:
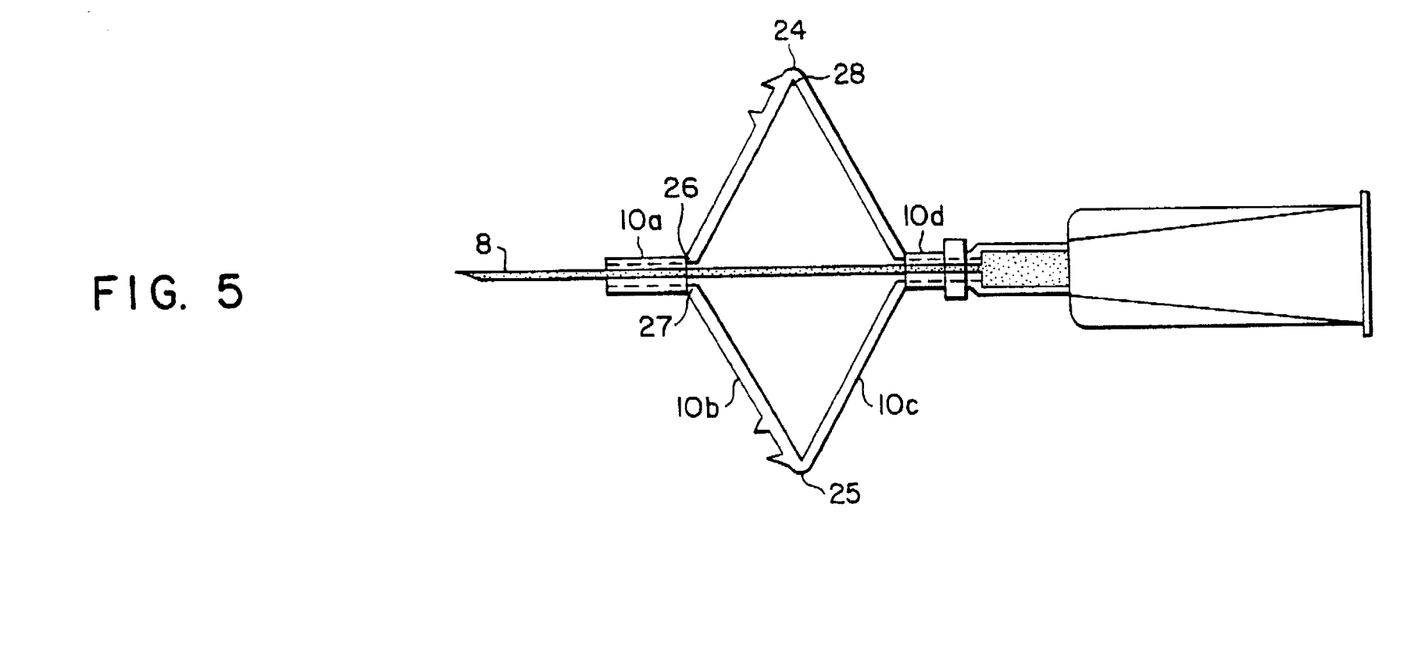
FIG. 5 illustrates the needle shield of the preferred embodiment of the present invention in an open position.

FIG. 5 illustrates sleeve 10 after an axial force exceeding the threshold has been applied. The displacement of the subportions of displaceable portions 10b and 10c of sleeve 10 allows the axial force to slidably move outer end portion 10a of the sleeve 10 axially along cannula 8, thereby facilitating insertion of the cannula 8 into the patient.

When the axial force is removed, such as when the cannula 8 is withdrawn from the patient, the compression force in hinge 28 creates a torque which causes the subportions of displaceable portions 10b and 10c of the sleeve 10 to return radially inwardly toward the cannula 8. This movement causes radially rigid outer end portion 10a to slide axially toward the tip of cannula 8 until the sleeve 10 reverts to the safe position as shown in FIG. 2 (i.e. rigid portion 10a is at least coextensive with, if not extending beyond, the tip end of cannula 8). Because most hypodermic needles currently in use are disposed of after one injection, fatigue of hinge 24 should not be a factor in preventing a compressive force from restoring the sleeve 10 to the safe position. The shield of the current invention may be optimized for use with hypodermic needles that are used numerous times, such as for catheters, if a suitable material is chosen for hinges 24, 25.

Figure 6:
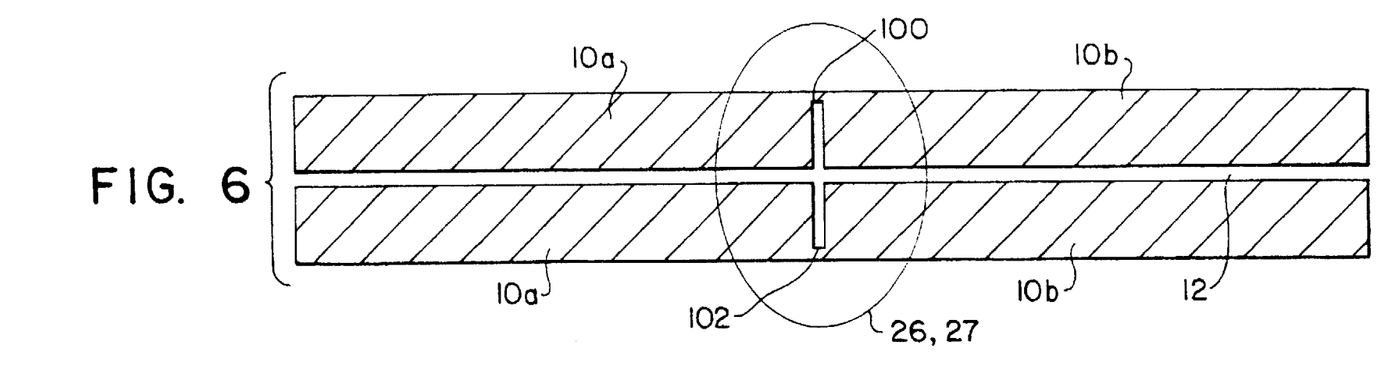
FIG. 6 illustrates a longitudinal cross-sectional exploded view of a hinging portion that joins a displaceable portion of the sleeve with a radially rigid portion of the sleeve.

As illustrated in FIG. 3, hinges 26, 27 and 30, 31 allow the subportions of slats 10b and 10c, respectively, to be radially displaced once the threshold axial force has been exceeded. Hinges 26, 27 may be implemented by forming slots 100, 102 in sleeve 10, as shown in FIG. 6. Hinges 30, 31 may be implemented in the same manner. Alternatively, if an increase in the initial rigidity is desired, no slots need be formed, and hinges 26, 27 and 30, 31 can be left to flex due to the inherent flexibility of the material from which sleeve 10 is made.

As shown in FIG. 5, in the preferred embodiment, hinges 26, 27 and 30, 31 exert equal axial forces to the slats 10b and 10c such that the subportions of slats 10b and 10c are radially displaced substantially equally from the cannula 8 upon application of an axial force that exceeds the threshold.

Figure 9:
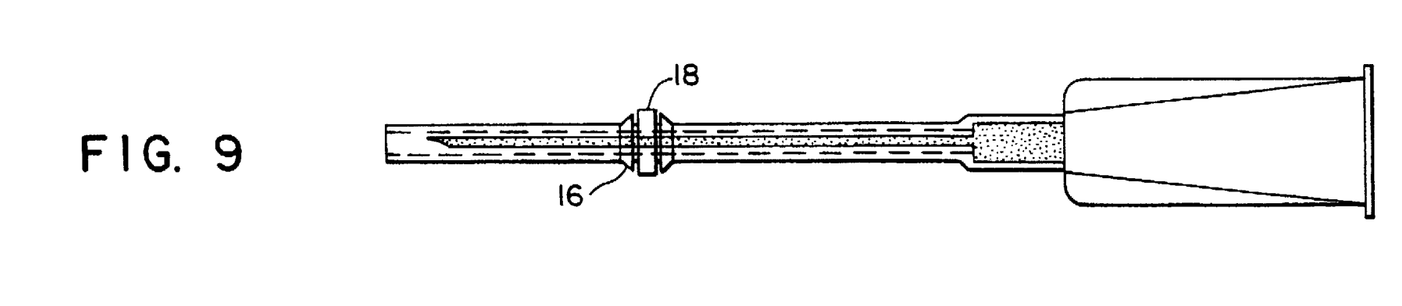
FIG. 9 illustrates the shield of the present invention in a safe and locked position.

The needle shield of the present invention as shown in FIG. 2 may be locked in the safe position to further increase the amount of axial force required to cause accidental exposure of the cannula 8, as well as to make illicit use after disposal difficult. FIG. 9 illustrates the needle shield of the present invention in a locked position. A collar index 16 consists of a first circumferential flange 16a, 16c, and a second circumferential flange 16b, 16d. As illustrated in FIG. 9, a collar 18 is disposed within the two flanges of this index to further resist displacement of the displaceable portions or slats 10b and 10c of the sleeve 10.

As illustrated in FIG. 3, the slat or displaceable portion 10b nearest the outer end of the sleeve 10 is preferably formed integrally with both of the circumferential flanges 16a, 16c, and 16b, 16d. The flanges forming collar index 16 vary in diameter such that in the cross-sectional view of FIG. 3, the borders or edges of the flanges appear as four right triangles 16a, 16b, 16c and 16d. The border of flange 16b, 16d facing toward inner end 10d of the sleeve 10 rises from a minimum value at a base point nearest the inner end of the sleeve to a maximum value at a point closer to the tip of the cannula 8.

As shown in the safe position of the needle shield in FIG. 1, the collar 18 is normally disposed at the inner end of sleeve 10 away from the tip of the cannula 8, and forms a diameter that is preferably just greater than that of the sleeve. To lock the shield, the needle administrator slides the collar 18 axially along the portion 10d of sleeve 10, past the hinges 24, 25, and partly over the slat 10b toward flange 16b, 16d. It will be noted that this is a direction opposite to that typically associated with accidental exposure to a used cannula. As the collar 18 is slid toward and engages the flange 16b, 16d, its diameter stretches slightly because of a distributed radial force created by the increasing diameter of the flange. The collar 18 stretches sufficiently to slide over the flange 16b, 16d, and then occupies the longitudinal space on the sleeve 10 between the two flanges 16b, 16d, and 16a, 16c. Once located between the two flanges in collar index 16, the collar resumes its normal diameter. Further axial movement of the collar 18 in either direction is then prevented by the two circumferential flanges.

In the locked position, if an axial force is applied to the sleeve 10 as illustrated in FIG. 3, the collar 18 prevents displacement of the displaceable portion or slat 10b of the sleeve 10 by applying a force, directed radially inward toward the cannula 8, to the displaceable portion 10b of the sleeve 10. If the collar 18 is made of sufficiently rigid material, the collar 18 will restrict radial movement of the slat 10b of the sleeve 10, even for large axial forces applied to the sleeve 10. Of course, collar 18 must be flexible enough to be stretchable over the flange 16b, 16d.

Figure 12A:
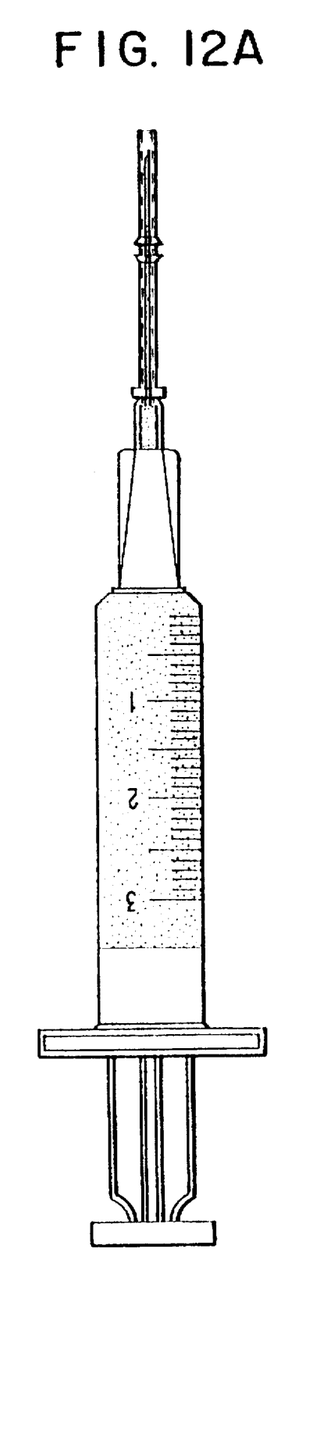
FIG. 12a illustrates the needle shield of the present invention in the safe position.
Figure 12B:
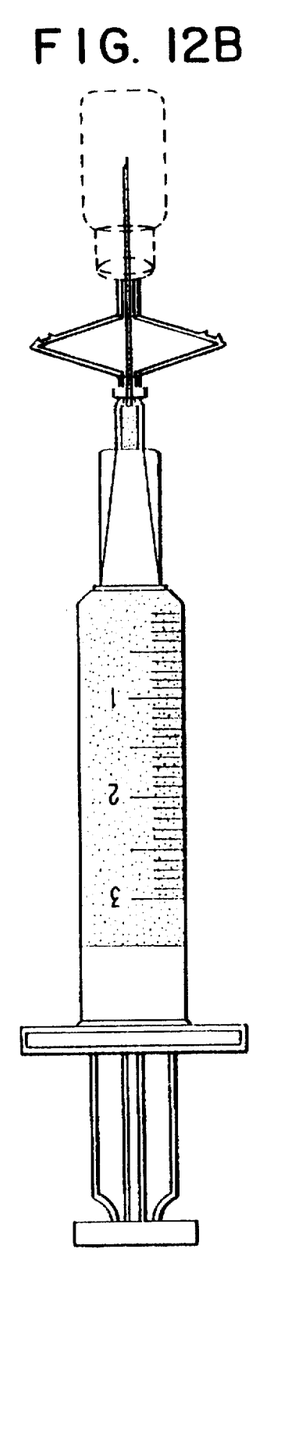
FIG. 12b illustrates the needle shield of the present invention in the exposed position under use.
Figure 12C:
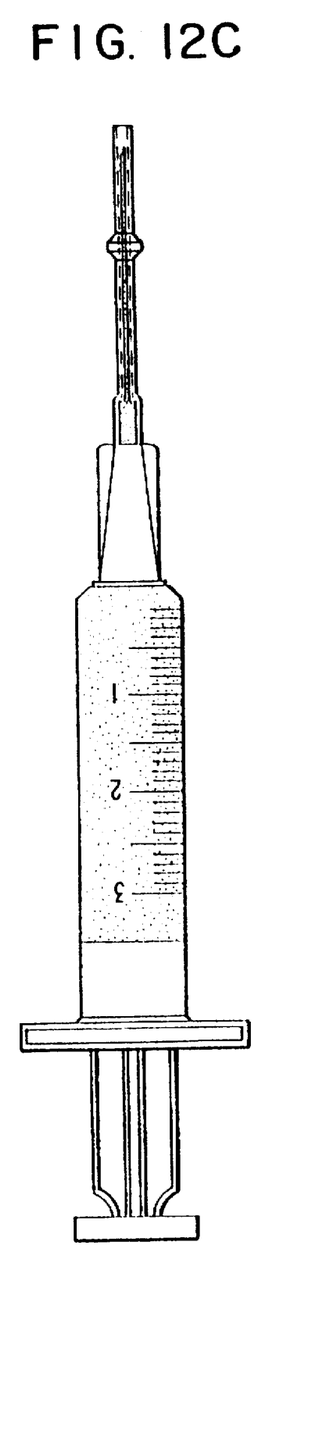
FIG. 12c illustrates the needle shield of the present invention in the safe and locked position.

While the needle administrator slides the collar 10, the cannula 8 remains completely housed within the sleeve 10 in the safe position. The operation of sliding the collar 18 towards the tip end of cannula 8 presents little risk of accidental exposure to the cannula 8. Should the needle administrator neglect to lock the shield in the safe position, accidental exposure to the cannula 8 is still prevented provided no axial force exceeding the threshold is applied. FIGS. 12a, 12b and 12c illustrate the shield of the present invention in the safe, the open, and the locked positions, respectively.

The collar index is designed to permit stretching of the collar such that the collar can be slipped over the border forming the index to engage the index. Once engaged, the collar snaps back to its original diameter and cannot be disengaged from the index. In this "locked" state, a force which greatly exceeds the threshold force of the "safe" position is required to expose the cannula because the collar prohibits displacement of the displaceable portions of the sleeve. Further, it discourages illicit use of the discarded needle by making exposure of the cannula extremely difficult.

Figure 7:
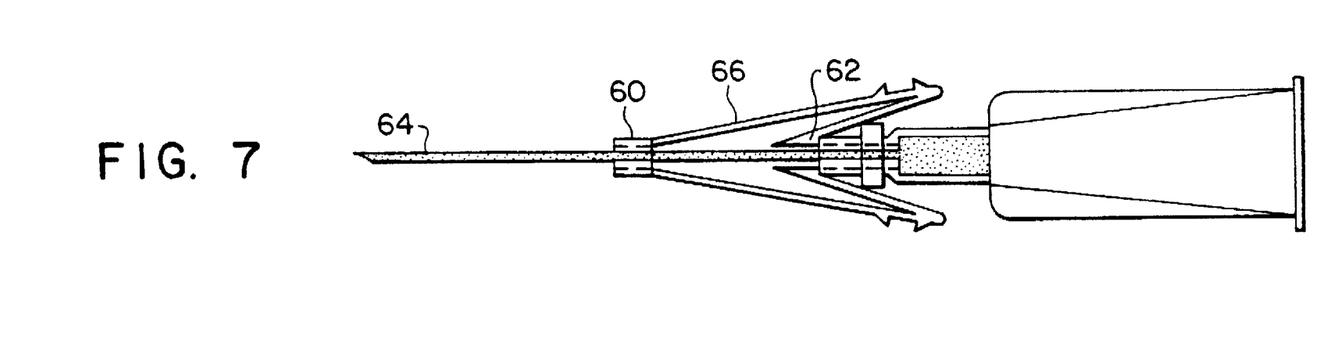
FIG. 7 illustrates an alternate embodiment of the sleeve of the present invention in an open position.
Figure 8:
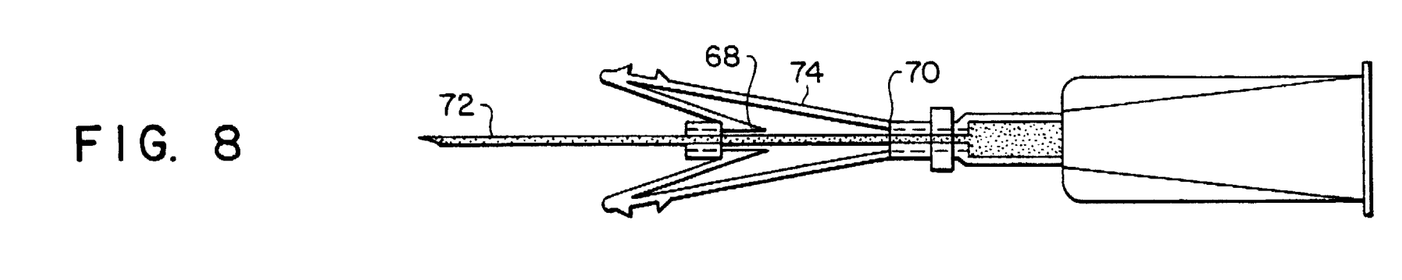
FIG. 8 illustrates another alternate embodiment of the sleeve of the present invention in an open position.

FIGS. 7 and 8 illustrate alternate embodiments of the hypodermic needle shield of the present invention. In the embodiment illustrated in FIG. 7, a hinging portion 60 of the sleeve 66 towards the tip end of cannula 64 provides a greater force than a hinging portion 62 away from the tip of the cannula 64. The unequal forces cause the forward end of sleeve 66 to move into the position as shown in FIG. 7.

Conversely, in the embodiment illustrated in FIG. 8, a hinging portion 68 of sleeve 70 towards the tip end of cannula 72 provides less force than a hinging portion 74 away from the tip end of cannula 72. The unequal forces cause sleeve 70 to move into the position as shown in FIG. 8. One or the other of these embodiments may be preferable depending on the geometry of the surface to which the cannula 64 or 72 is to be applied.

If hinging portions 26, 27 (and 30, 31) are implemented by forming slots 100, 102 as illustrated in FIG. 6, the hinging portions may be manufactured to present unequal reactive forces by forming a slot of greater length for one hinging portion than another; each hinging portion will provide a resistance to motion that is inversely proportional to the length of the associated slot. Alternatively, one hinging portion may include a slot while the other hinging portion does not include a slot. The hinging portion implemented with a slot will present less resistive force than the hinging portion not including a slot. Alternatively, hinging portions may be implemented by forming angled slots to influence the direction of displacement.

In another embodiment, hinging portions may provide unequal forces by narrowing the sleeve 10 at one hinging portion either more or less than at the other hinging portion. The hinging portion formed at the narrower part of the sleeve 10 will provide less resistive force than the other hinging portion. Finally, in a unitary sleeve is not employed, hinging portions may be manufactured to provide unequal forces by using different materials to form the different hinging portions.

Those of skill in the art will recognize that there are many variables in the manufacturing process that can be altered to achieve different performance points. Rigidity and elasticity of the materials used to form the sleeve, the dimensions of the sleeve, the characteristics of the hinging portions, the number of subportions into which the displaceable portions are divided, etc. can all be varied to produce a different threshold of displacement forces, different force versus displacement characteristics, and the amount of compressive force available to return the sleeve to a safe position after withdrawal of the applied axial force from the shield. The preferred embodiment is disclosed as being unitary in nature, i.e., axially rigid portions 10a, 10d, displaceable portions 10b, 10c and hinging portions 24, 25, 26, 27, 30 and 31 are all of integrated construction. It is conceivable, however, that some or all of the components of sleeve 10 can be separate and distinct. Of course, the hinging portions can be made out of more commonly known hinge mechanisms. So long as the above-contemplated variations of the preferred embodiment provide the desired characteristics: 1) an initial threshold force that must be exceeded for displacement of the sleeve can begin; 2) a force versus displacement curve that does not greatly exceed the threshold force over the desired range of displacement, and 3) a sufficient compressive force in the hinging portions of the sleeve to return the sleeve to the safe position upon removal of the force, these variations will fall within the intended scope of the present invention.

Figure 11A:
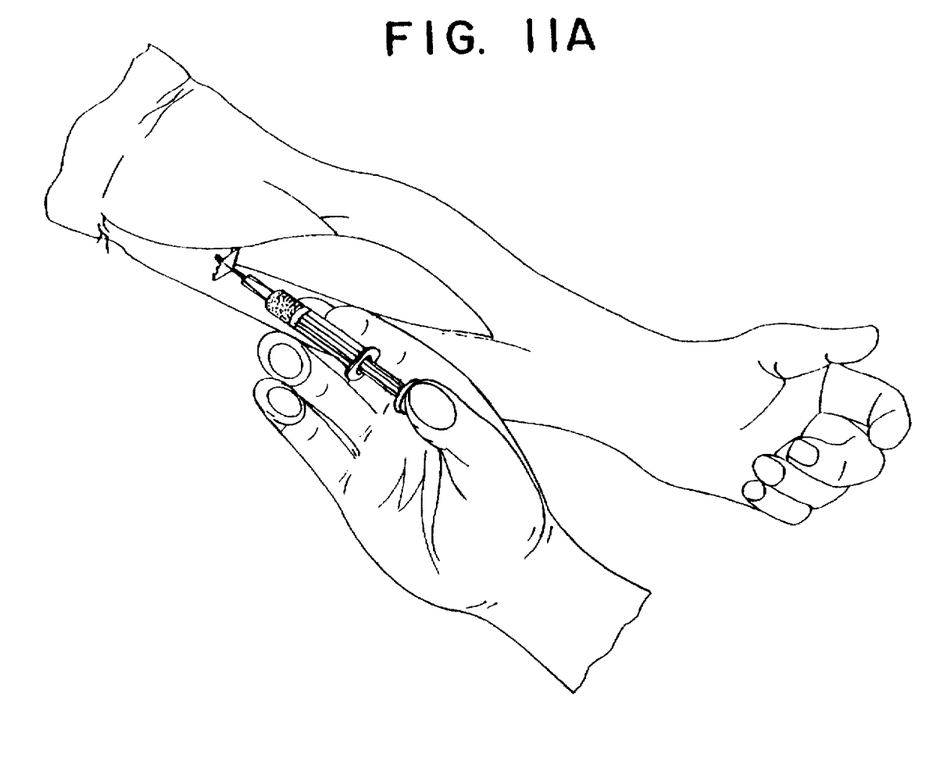
FIG. 11a illustrates a hypodermic needle in conjunction with the needle shield of the present invention being administered to a patient.
Figure 11B:
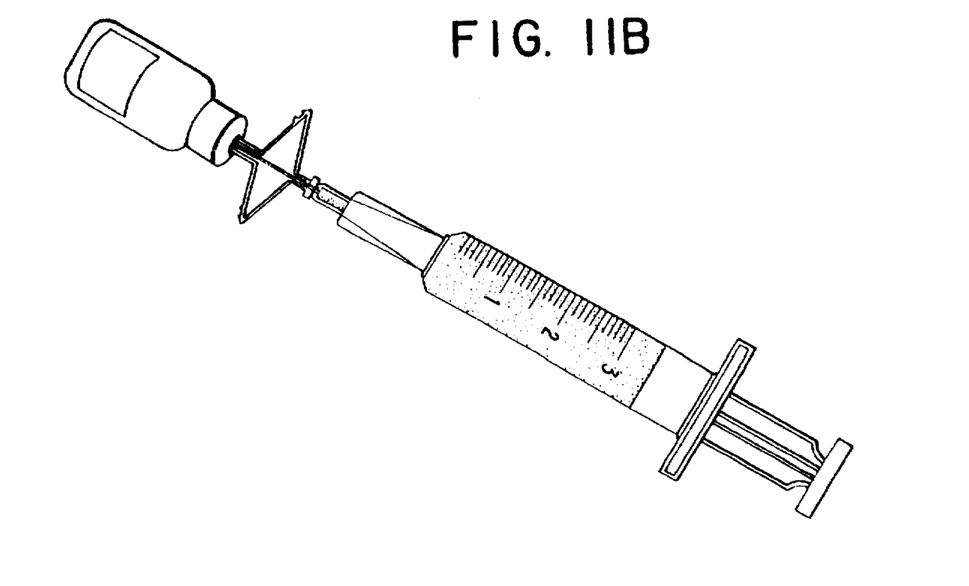
FIG. 11b illustrates a hypodermic needle and shield of the present invention as the needle is being filled from a vial.

The invention thus provides a hypodermic needle that will not be exposed unless a force is applied that exceeds some threshold. Unlike prior art devices, particularly those using springs, once the threshold force is exceeded, little additional force (if any) is required to cause further displacement of the shield and thus further exposure of the cannula 8. As shown in FIG. 11a, when a needle administrator applies the threshold force against a patient, the cannula 8 is inserted into the patient. The same is true when withdrawing drug from a vial as shown in FIG. 11b. When the needle administrator stops applying an axial force and withdraws the cannula 8 from the patient, the cannula retracts into the sleeve 10. Once the cannula 8 is completely withdrawn from the patient, the cannula 8 is completely retracted into the sleeve 10 and the hypodermic needle shield is again in the safe position. Thus, the tip of the cannula 8 is exposed to the patient only during insertion and withdrawal of the needle, protecting needle administrators and others from accidental exposure to the tip of cannula 8.

Figure 10A:
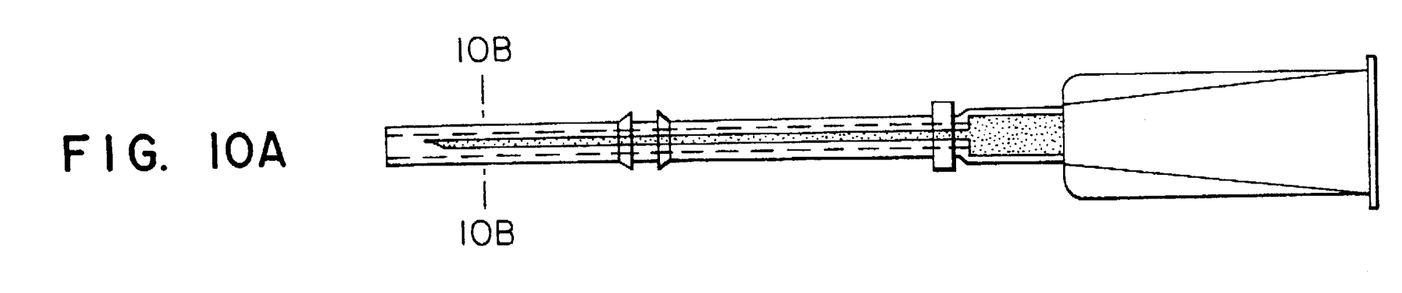
FIG. 10a illustrates channels that may be employed to divert excess blood from a cannula.
Figure 10B:
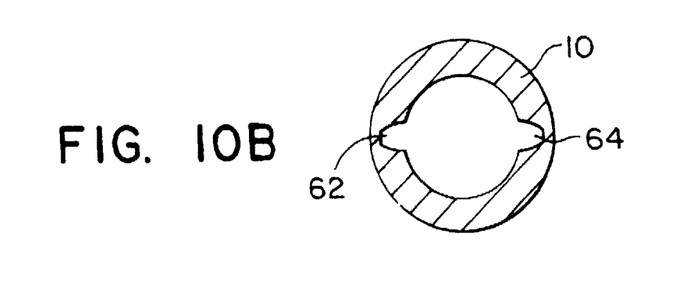
FIG. 10b illustrates the channels as a cross-sectional view through lines A—A.

To help prevent exposure to blood adhering to the cannula 8 as a result of insertion into a patient, one or more channels 62 and 64 may be formed in the sleeve 10 as shown in FIGS. 10a and 10b. As the anterior or forward end of the sleeve 10 moves along the cannula 8, excess blood will tend to gather inside the channels 62 and 64 rather than being forced outward through the end of sleeve 10.

In addition to the previously mentioned benefits, the needle shield of the present invention is easier to manufacture than prior art needle shields. Prior art needle shields typically contain many moving pieces. The hub 14 and the sleeve 10 of the present invention may be manufactured as a single unitary piece by a simple molding process, requiring only the recurring of an existing mold cavity. The cannula is inserted after the molding process and attached in the normal manner with, at most, a few minor modifications. The collar 18 and the collar index 16 may also be assembled with the hub 14 and the sleeve 10 during the molding process. Thus, the shield of the present invention may be manufactured by a simple molding process that avoids expensive assembly procedures.

Figure 13A:
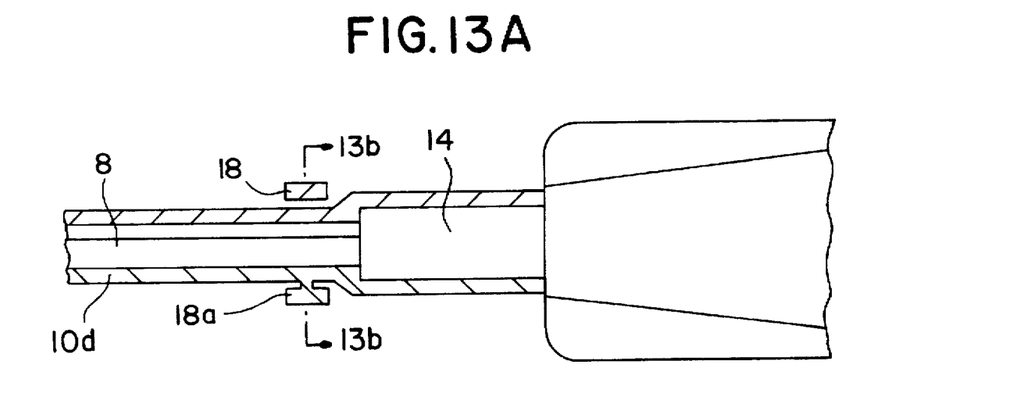
FIG. 13a is an enlarged fragmentary longitudinal view, partially in cross-section, illustrating the frangible connection of the slidable collar to the flexible sleeve.
Figure 13B:
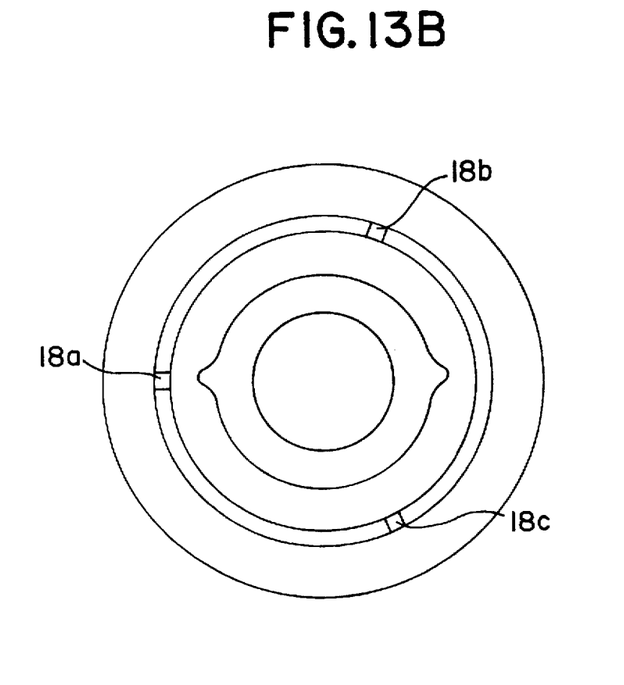
FIG. 13B is a transverse cross-sectional view taken on line A—A of FIG. 13A and further showing both the frangible fingers supporting the collar and the fluid channels.

According to the presently preferred form of the invention the collar 18 is made integral with the other parts of the needle shield. As shown in FIGS. 13a and 13b, the collar 18 is essentially in the form of an annular band with its interior wall surface spaced slightly away from the wall of the sleeve. At three points spaced 120 degrees around its circumference the collar 18 is frangibly connected to the sleeve 10d by means of small fingers 18a, 18b, 18c. These fingers are formed in the molding process, along with the sleeve and the collar itself. In operation, the size and strength of the fingers are sufficiently small that the collar can be separated from the sleeve, and slid toward the slat 10b, all as previously described.

The present invention may be manufactured using other efficient techniques. For example, the needle shield of the present invention may also be coupled to existing hypodermic needle hubs by heat sealing or sonically melting the sleeve 10. Thus, an existing hypodermic needle manufacturer need not redesign a needle assembly to operate in conjunction with the shield of the present invention.

The invention has been described in conjunction with numerous preferred embodiments. Numerous alternatives, modifications, variations and uses will be apparent to those skilled in the art in light of the foregoing description. For example, the indentation of hinging portions 24, 25 may be formed of shapes other than a triangle, such as a semi-circle. Also, instead of being formed by an indentation, hinging portions 24, 25 may be formed by joining subportions of displaceable portions 10b and 10c at an angle. Similarly, hinging portions 26, 27 and 30, 31 need not be implemented with slots. The shield of the present invention need not be formed as a unitary sleeve and many materials, other than those disclosed herein, will be recognized by those of skill in the art as suitable for constructing the sleeve.

What we claim is:

1. A shield for a hypodermic needle assembly that includes a needle having a base end, a main portion, and a tip end, said shield comprising:

a hollow sleeve made of a plastic material, having a rigid inner end portion adapted to be coupled to the base end of the needle, an elongated main portion adapted to normally enclose the main portion of the needle, and a slidable outer end portion adapted to normally extend beyond the tip end of the needle;

said elongated main portion of said hollow sleeve being responsive to an axial force on said outer end portion of said sleeve for expanding radially outwardly and thereby slidably retracting said end portion of said sleeve and exposing the needle tip end;

said elongated main portion of said sleeve also having a spaced pair of circumferential flanges formed thereon; and a flexible collar encircling said sleeve and normally disposed adjacent said inner end portion thereof;

so that when an injection is to be administered into a body and an axial force is applied to said outer end portion of said sleeve to slidably expose the needle, and subsequent withdrawal of the needle assembly from the body allows said elongated main portion of said sleeve to resume its original shape, said collar may then be transported axially from said inner end portion of said sleeve and over one of said flanges so as to occupy a position between said pair of flanges and thereby prevent both the subsequent expansion of said elongated main portion of said sleeve and any subsequent exposure of the needle.

2. A needle shield as defined in claim 1 wherein the circumferential flange closer to said inner end of said shield has a sloping outer side wall facing toward said inner end of said shield, to facilitate the stretching of said flexible collar over said side wall.

3. A needle shield as defined in claim 1 wherein said elongated main portion of said sleeve has a plurality of longitudinal slits formed therein providing a plurality of longitudinal slats.

4. A needle shield as defined in claim 3 wherein there are two of said longitudinal slits and two of said longitudinally extending displaceable portions of said sleeve.

5. A shield for a hypodermic needle assembly that includes a needle having a base end, a main portion, and a tip end, said shield comprising:

a hollow sleeve made of a plastic material, having a rigid inner end portion adapted to be coupled to the base end of the needle, an elongated main portion adapted to normally enclose the main portion of the needle, and a slidable outer end portion adapted to normally extend beyond the tip end of the needle;

said elongated main portion of said hollow sleeve having a longitudinal mid-region, and a pair of longitudinally spaced circumferential flanges formed on said mid-region;

said elongated main portion of said sleeve also having a plurality of longitudinal slits formed therein providing a plurality of longitudinal slats, so as to be responsive to an axial force on said outer end portion of said sleeve for expanding radially outwardly and thereby contracting its length and slidably retracting said outer end portion of said sleeve and exposing the needle tip end; and a flexible collar encircling said sleeve and normally disposed adjacent said inner end portion thereof;

so that when an injection is to be administered and an axial force is applied to said outer end portion of said sleeve to slidably expose the needle, and subsequent withdrawal of the needle assembly allows said sleeve to resume its original shape and thereby slidably cover the needle tip end with said outer end portion of said sleeve, said collar may then be moved axially from said inner end portion of said sleeve and over one of said flanges so as to occupy a position between said pair of flanges and thereby prevent both the subsequent expansion of said mid-region of said sleeve and any subsequent exposure of the needle.

6. A needle shield as defined in claim 5 wherein the circumferential flange closer to said inner end of said shield has a sloping outer side wall facing toward said inner end of said shield, to facilitate the stretching of said flexible collar over said side wall.

7. A needle shield as defined in claim 5 wherein there are two of said longitudinal slits and two of said longitudinally extending displaceable portions of said sleeve.

8. A shield for a hypodermic needle assembly that includes a needle having a base end, a main portion, and a tip end, said shield comprising:

a hollow sleeve made of a plastic material, having an inner end portion adapted to be coupled to the base end of the needle, an elongated main portion adapted to enclose the main portion of the needle, and an outer end portion adapted to normally extend beyond the tip end of the needle;

said elongated main portion of said hollow sleeve having a plurality of longitudinal slits formed therein to thus provide a plurality of longitudinally extending portions thereof which are laterally displaceable;

each of said longitudinally extending displaceable portions on its radially inward surface being partially cut away adjacent both said inner and outer end portions of said sleeve and also having a transverse triangular portion thereof cut away at an intermediate location along its length, so as to permit all of said displaceable portions of said sleeve to expand laterally outwardly at said intermediate location;

said displaceable portions of said sleeve also having a spaced pair of exterior circumferential flanges formed thereon adjacent said intermediate location; and a flexible collar encircling said sleeve adjacent said inner end thereof and movable to a position between said flanges;

so that when an axial force is applied to said outer end of said sleeve to slidably expose the needle, and subsequent withdrawal of the needle allows said sleeve to resume its original shape at said intermediate location, said collar may then be axially slid from said inner end of said sleeve and over the nearer one of said flanges so as to occupy a position between said flanges and thereby prevent both the subsequent expansion of said sleeve and any subsequent exposure of the needle.

9. A needle shield as defined in claim 8 wherein all of said triangular cutaway portions are longitudinally aligned.

10. A shield for a hypodermic needle assembly that includes a needle having a base end, a main portion, and a tip end, said shield comprising:

a hollow sleeve made of a plastic material, having a rigid inner end portion adapted to be coupled to the base end of the needle, an elongated main portion adapted to enclose the main portion of the needle, and an outer end adapted to normally extend beyond the tip end of the needle;

said elongated main portion of said hollow sleeve having a plurality of longitudinal slits formed therein to weaken its structure so as to be responsive to an axial force on said outer end thereof for expanding the longitudinal mid-region of said sleeve main portion outwardly and exposing the needle tip end;

said longitudinal mid-region of said sleeve also having a spaced pair of circumferential flanges formed thereon; and a flexible collar encircling said sleeve adjacent said inner end portion thereof;

so that when an injection is to be administered and an axial force is applied to said outer end of said sleeve to slidably expose the needle, and subsequent withdrawal of the needle assembly allows said longitudinal mid-region of said sleeve to resume its original shape, said collar may then be axially slid from said inner end portion of said sleeve and over one of said flanges so as to occupy a position between said pair of flanges and thereby prevent both the subsequent expansion of said sleeve and any subsequent exposure of the needle.

11. A needle shield as defined in claim 10 wherein the circumferential flange closer to said inner end of said shield has a sloping outer side wall facing toward said inner end of said shield, to facilitate the stretching of said flexible collar over said side wall.

12. A needle shield as defined in claim 10 wherein there are two of said longitudinal slits and two of said longitudinally extending displaceable portions of said sleeve.

13. A shield for a hypodermic needle assembly that includes a needle having a base end, a main portion, and a tip end, said shield comprising:

a hollow sleeve made of a plastic material, having a rigid inner end portion adapted to be coupled to the base end of the needle, an elongated main portion adapted to normally enclose the main portion of the needle, and a slidable outer end portion adapted to normally extend beyond the tip end of the needle;

said elongated main portion of said hollow sleeve having a longitudinal mid-region, and a pair of longitudinally spaced circumferential flanges formed on said mid-region;

said elongated main portion of said sleeve also having a plurality of longitudinal slits formed therein providing a plurality of longitudinal slats, so as to be responsive to an axial force on said outer end portion of said sleeve for expanding radially outwardly and thereby contracting its length and slidably retracting said outer end portion of said sleeve and exposing the needle tip end; and a flexible collar encircling said sleeve and normally disposed adjacent said inner end portion thereof;

so that when an injection is to be administered an axial force is applied to said outer end portion of said sleeve to slidably expose the needle, and subsequent withdrawal of the needle assembly allows said sleeve to resume its original shape and thereby slidably cover the needle tip end with said outer end portion of said sleeve, said collar may then be moved axially from said inner end portion of said sleeve and over one of said flanges so as to occupy a position between said pair of flanges and thereby prevent both the subsequent expansion of said mid-region of said sleeve and any subsequent exposure of the needle.

14. A needle shield as defined in claim 13 wherein a plurality of channels are formed in the inner wall surfaces of said sleeve.

\* \* \* \* \*